(12) United States Patent
Lord

(10) Patent No.: US 6,210,391 B1
(45) Date of Patent: Apr. 3, 2001

(54) RAPID TRANSFER AUTOTRANSFUSION BAG AND METHODS RELATED THERETO

(75) Inventor: Kevin M. Lord, East Taunton, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/370,967

(22) Filed: Aug. 10, 1999

Related U.S. Application Data

(60) Provisional application No. 60/109,099, filed on Nov. 19, 1998.

(51) Int. Cl.$^7$ .................................................. A61B 19/00
(52) U.S. Cl. ........................................... 604/403; 604/408
(58) Field of Search ................................ 604/403, 408, 604/615, 317; 220/9.1, 9.2, 495.01, 23.91; 222/92, 95, 103, 206, 210, 214

(56) References Cited

U.S. PATENT DOCUMENTS

| | | |
|---|---|---|
| Re. 27,132 | 6/1971 | Ilg . |
| 2,766,907 | 10/1956 | Wallace . |
| 3,054,401 | 9/1962 | Gewecke . |
| 3,228,395 | 1/1966 | Gewecke . |
| 3,335,912 | 8/1967 | Reeves . |
| 3,399,040 | 8/1968 | Ilg . |
| 3,888,239 | 6/1975 | Rubinstein . |
| 4,041,944 | 8/1977 | Rhodes . |
| 4,270,533 | 6/1981 | Andreas . |
| 4,337,769 | 7/1982 | Olson . |
| 4,564,359 | 1/1986 | Ruhland . |
| 4,573,992 | 3/1986 | Marx . |
| 4,798,578 | 1/1989 | Ranford . |
| 4,976,707 | 12/1990 | Bodicky et al. . |
| 5,074,839 | 12/1991 | Choksi et al. . |
| 5,472,420 | 12/1995 | Campbell . |

FOREIGN PATENT DOCUMENTS

| | | |
|---|---|---|
| 2 006 054 | 8/1971 | (DE) . |
| 295 18 561 U1 | 1/1996 | (DE) . |
| 2 677 887 | 12/1992 | (FR) . |
| 2 693 111 | 1/1994 | (FR) . |
| WO 89/07459 | 8/1989 | (WO) . |

*Primary Examiner*—Glenn K. Dawson
*Assistant Examiner*—Catherine Serke
(74) *Attorney, Agent, or Firm*—Richard D. Allison; Thomas J. DesRosier, Jr.

(57) ABSTRACT

Featured is a rapid transfer autotransfusion device and a system using such a device. Also featured are methods related to the collection and/or the re-infusion of collected blood to a patient. The autotransfusion device includes an actuator handle assembly having two arms, a top plate, a bottom plate and a flexible container secured to and between opposing surfaces of the top and bottom plates. The bottom plate includes a projection from two opposing sides thereof, that each rotatably engage a lower portion of an actuator handle arm. The actuator handle rotates about the bottom plate projections between a first position and a second position. The actuator handle further includes a follower member, having a first and second portion, and a displacing mechanism that is disposed in at least one actuator handle arm, more particularly, disposed in each actuator handle arm. The first portion of each follower member movably engages a portion of the top plate as the actuator handle moves between the first and second position. The displacing mechanism is configured to act on the second portion of the follower member at least when the actuator handle is moved to the second position so the follower member first portion is movably displaced thereby and so the opposing surface of the top plate is displaced with respect to the opposing surface of the bottom plate.

28 Claims, 9 Drawing Sheets

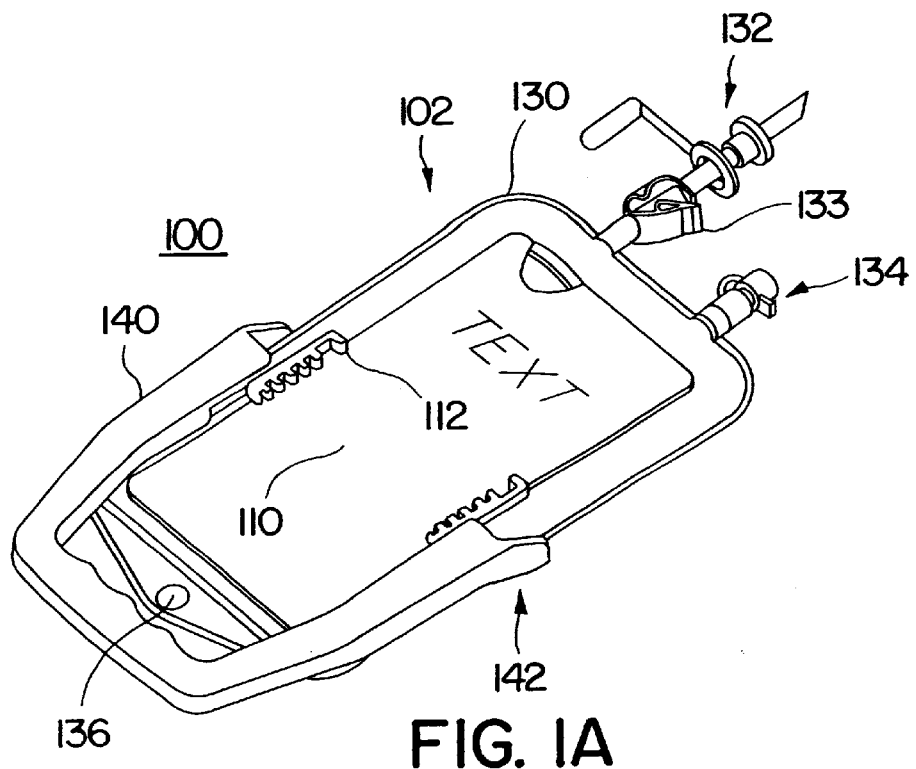
FIG. IA
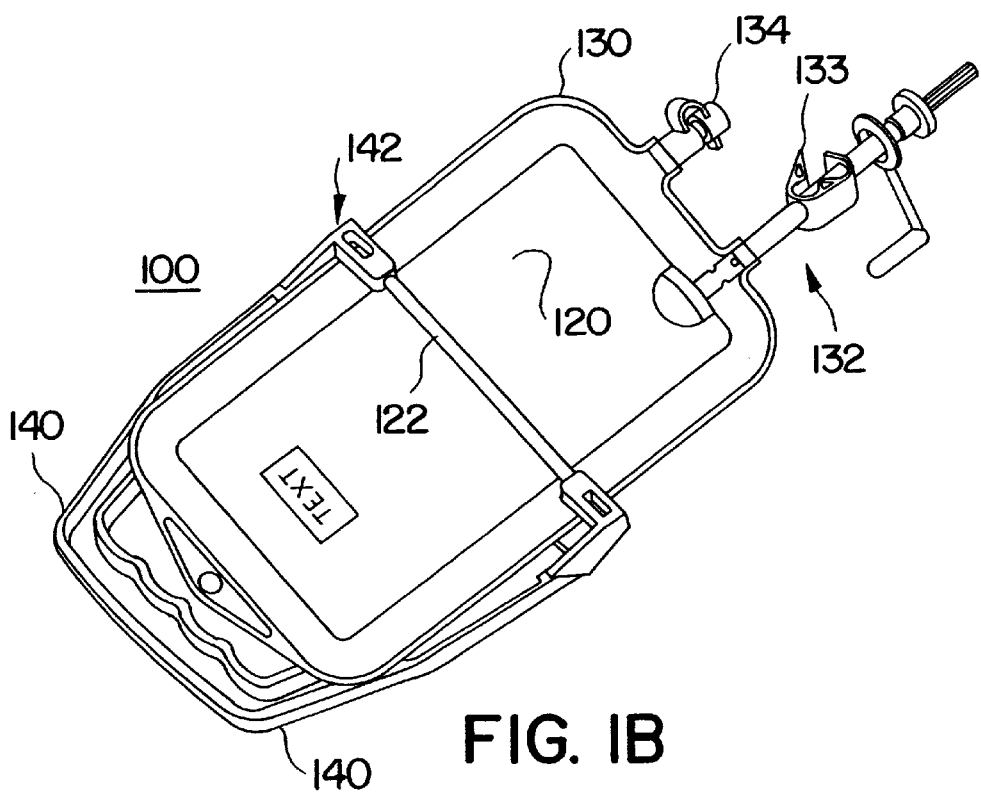
FIG. IB

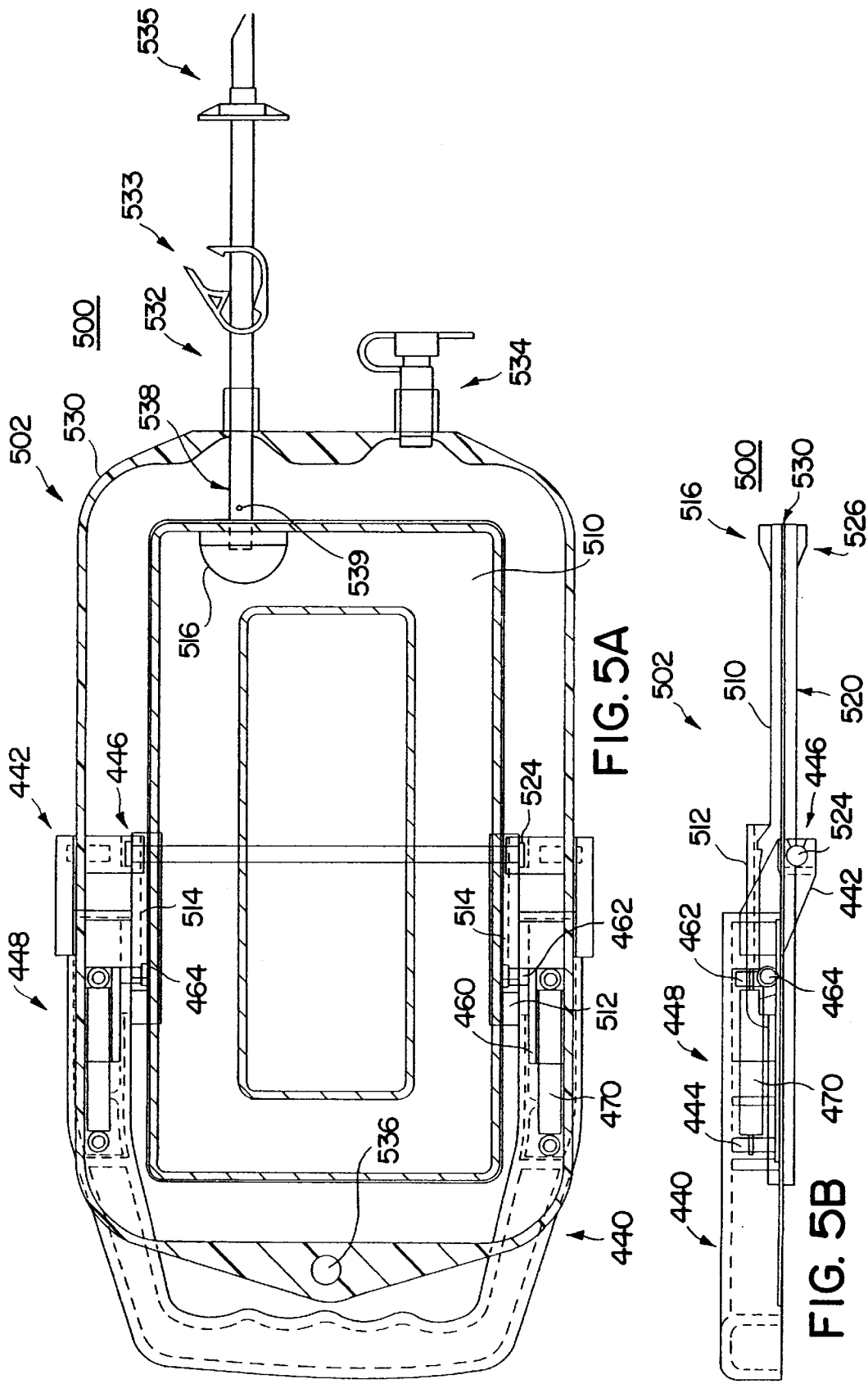

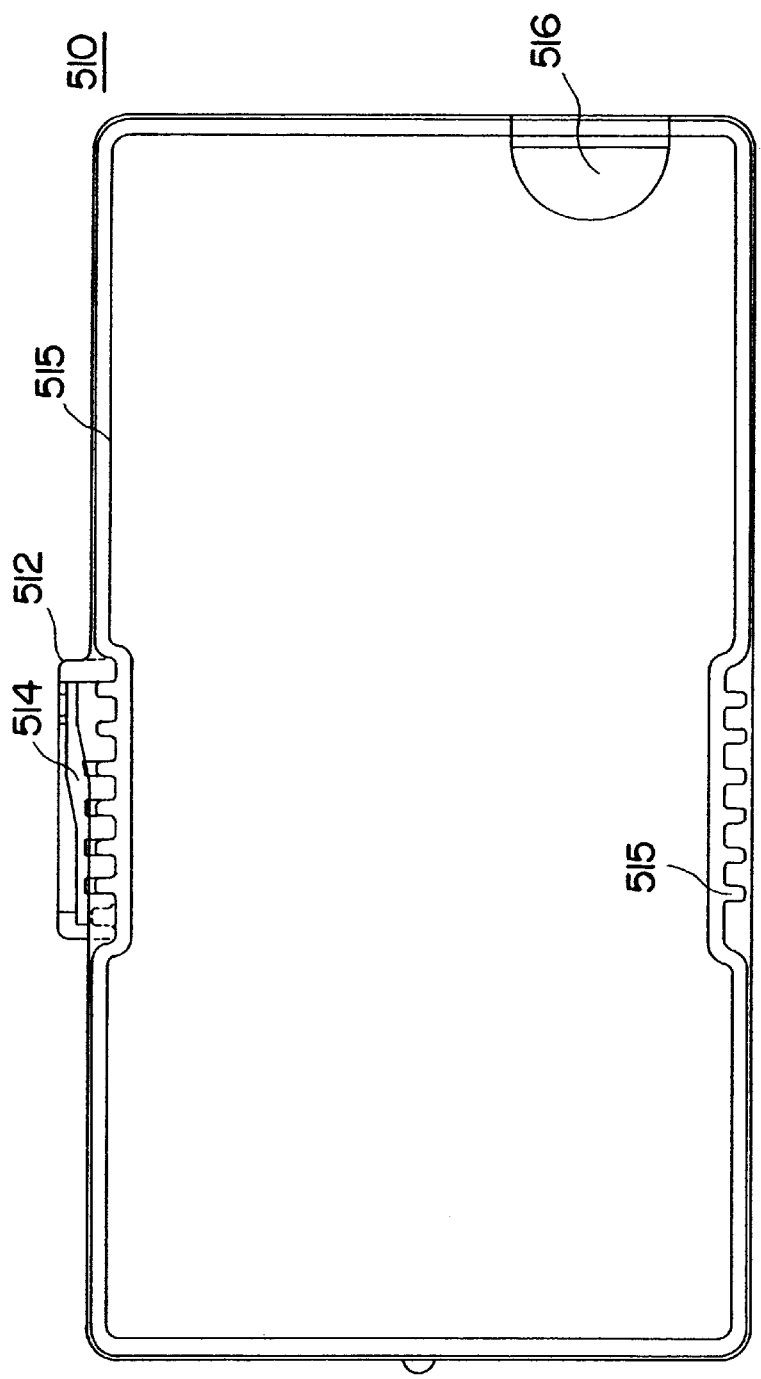
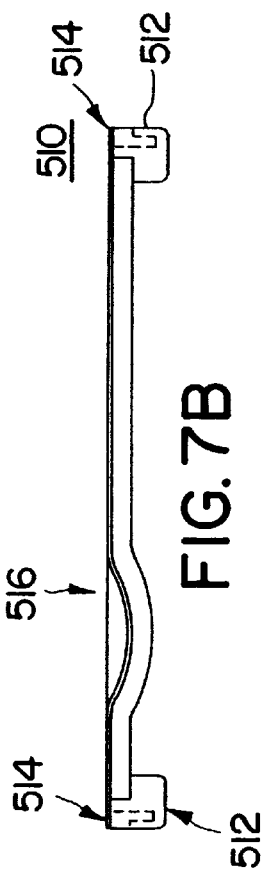
FIG. 7A
FIG. 7B

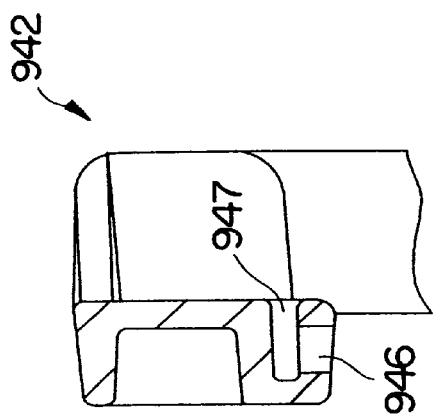
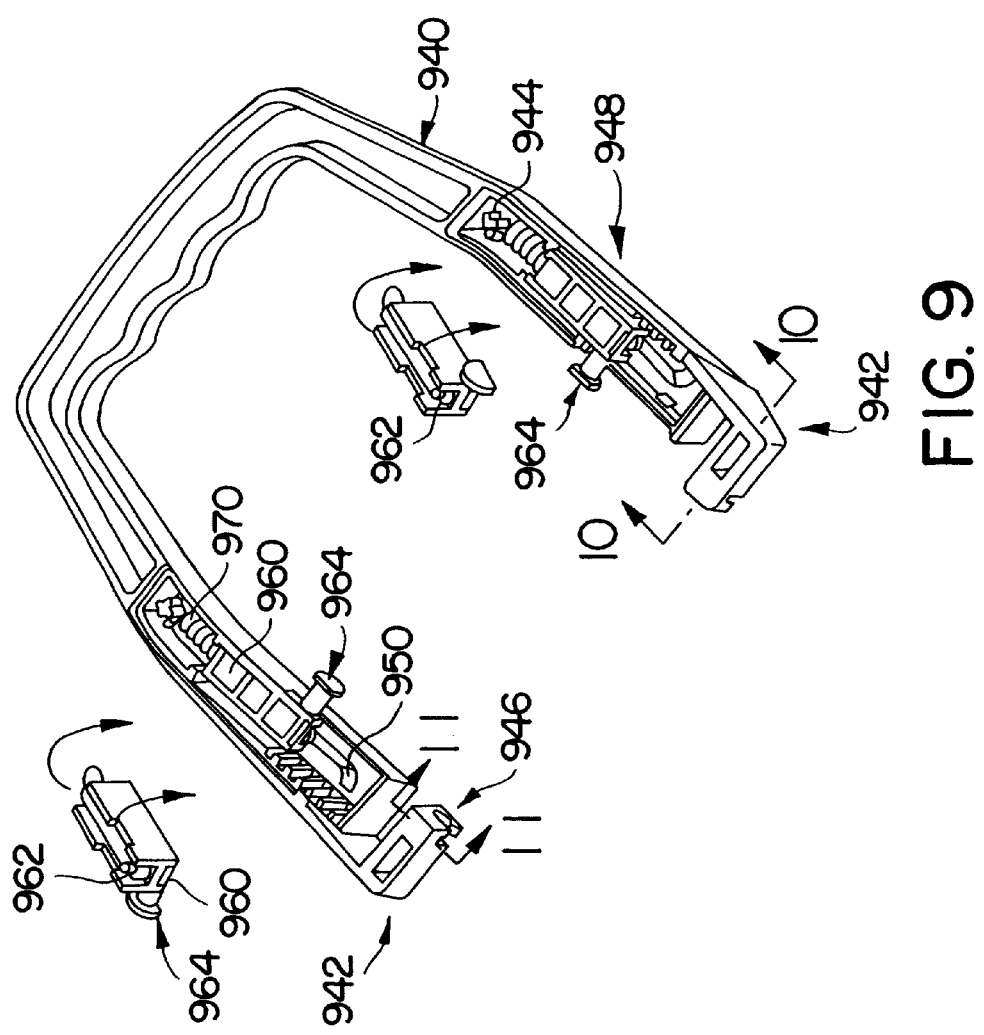

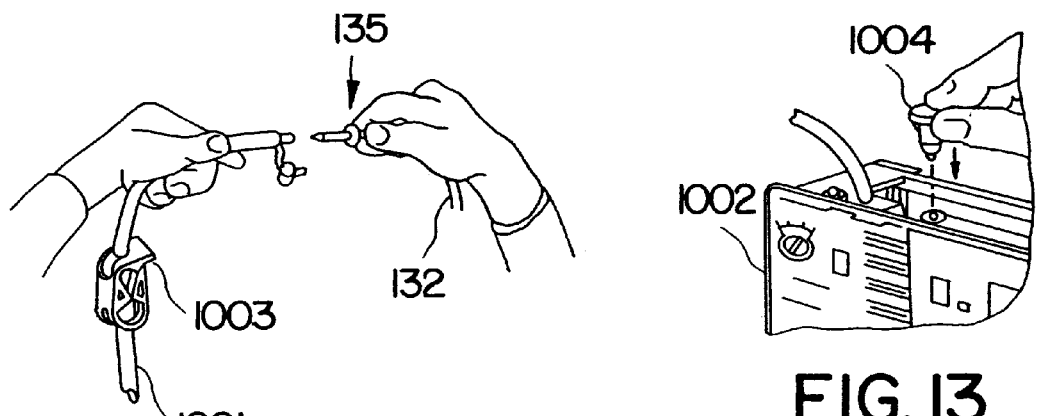
FIG. 12
FIG. 13
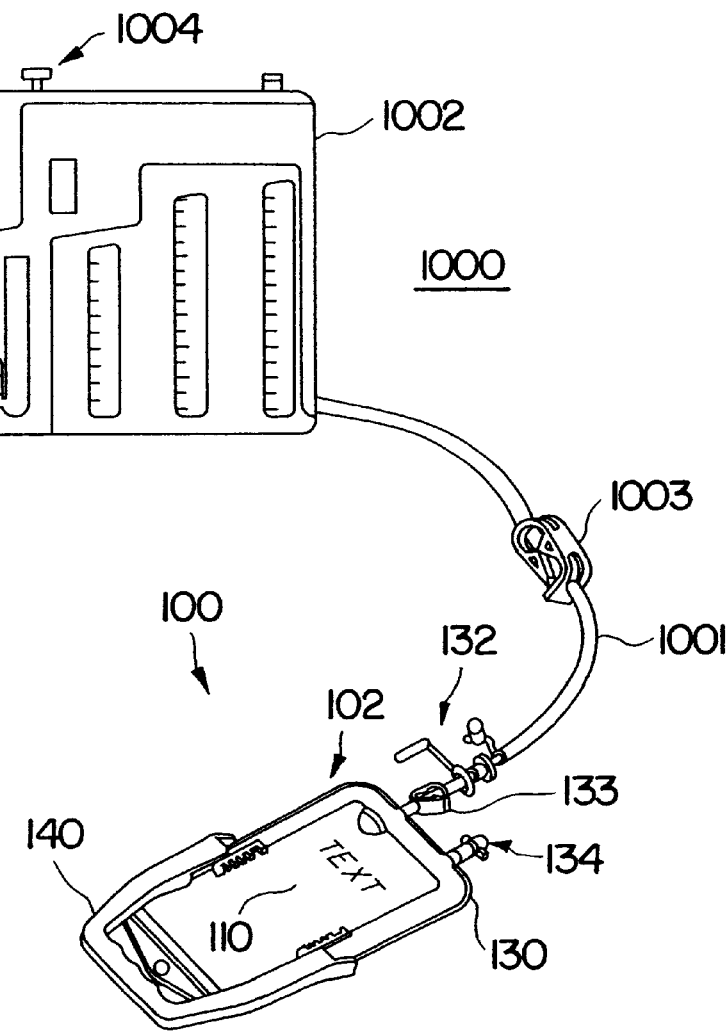
FIG. 14

RAPID TRANSFER AUTOTRANSFUSION BAG AND METHODS RELATED THERETO

The present application is related to U.S. Ser. No. 60/109,099 filed on Nov. 19, 1998 and the priority thereof is claimed hereby.

FIELD OF INVENTION

The present invention generally relates to devices for collecting blood and for re-infusing the collected blood back into a patient and more particularly to blood collection bags which can be used to re-infuse the blood by a gravity feed or under pressure.

BACKGROUND OF THE INVENTION

A number of devices or apparatuses have been developed to collect blood from the body cavity of a patient into a remotely located device and then to re-infuse the collected blood back into the patient. This practice has been found to be beneficial and advantageous in a number of respects and circumstances. A number of the remotely located devices may generally be categorized as a collection bag in which the blood is collected and which is then used later as the source of blood for re-infusion. There are, however, a number of shortcomings with such prior art collection bags as will be explained on connection with the following examples.

Three different devices for the collection and reinfusion of blood are described in U.S. Pat. No. 4,573,992 granted to Marx. For one such device (See FIG. 1 & 1a thereof) a flexible collection bag is housed within a rigid receptacle, where blood is collected in the flexible bag by creating suction forces within the flexible bag. U.S. Pat. No. 5,275,585 granted to Olson also discloses another device that employs a flexible container or bag within a rigid outer container. Prior to use, the flexible bag is expanded so it generally conforms to the interior surface of the rigid receptacle. Also, a through aperture is described in the rigid container that communicates with the space between the flexible bag and the rigid container is sealed off or is interconnected to a suction source. In this way, when suction forces are established within the flexible bag, the bag will not collapse. It is further described that following collection of blood, the through aperture can be interconnected to a pressure source so the blood can be re-infused under pressure.

Such devices are cumbersome. Also the container within a container design of these devices makes it difficult to quickly and accurately determine the amount of blood that was collected in the flexible bag and then re-infused back into the patient. Also, proper operation of these devices requires that the interior of the rigid container does not communicate with outside air and/or is interconnected to a suction source. As such, pressure tight conditions must be established for all the penetrations through the housing. This increases the complexity and use of the device. Also, in some cases reduced pressure conditions in the space between the rigid container and outside the flexible bag are established to create the suction forces within the flexible bag.

The other embodiments described in U.S. Pat. No. 4,573,992 (see FIGS. 2 & 3 thereof) employ a concertina-like container having two ports at opposite ends of the container. In an embodiment shown in FIG. 2 of this patent, one port is interconnected to a drain line from the patient and the other port is interconnected to a suction source. Also, the concertina-like structure is configured so it does not compress substantially in the radial direction when a reduced pressure condition is established within the container but the container may be compressed in the axial direction. This embodiment further includes a rigid frame structure that is external to the container and extends axially between the two ports, and which cooperates with the configuration of each port to keep the concertina-like container in an extended condition while collecting blood. After the container is filled and after the container has been appropriately reconnected for re-infusion, the rigid structure is removed and the concertina-like container is mechanically or manually compressed axially to force the blood out of the container.

In a further embodiment shown in FIG. 3 of the Marx patent, the concertina-like structure is configured to have an inherent resiliency so it will automatically expand axially and return to its expanded condition after it has been axially compressed. It is further provided that a spreading spring means, extending between the two ports, can be provided to augment or replace the inherent resiliency of the concertina-like container. In use, the container is compressed axially to its minimum volume by an external force and the suction port of the container is interconnected to a clamped off suction line to the body cavity. The clamp is slowly released and the inherent resiliency of the container and/or the spreading spring means causes the container to extend axially thereby drawing blood therein. After the container is filled with blood, the container is mechanically or manually compressed so as to force the blood out of a separate port in the container to enable the blood to be pressure re-infused into the patient.

The concertina-like container devices disclosed in the Marx patent are cumbersome and not easy to use. Also, these devices are configured to be used in pressurized re-infusion applications and do not lend themselves to gravity feed applications. In order to gravity feed using a concertina-like container, it would be necessary to vent the container while the blood is being removed. As to the second embodiment in the Marx patent and because of the design and intended use of this embodiment, the device is also configured with internal check valves to prevent, for example, the admission of air through one of the ports when drawing blood into the container. Such check valves and other design features of the second embodiment increase the manufacturing complexity of the device. Notwithstanding these check valves, it is still possible for air to be drawn into the container for example, by drawing in both blood and air from the body cavity. Thus, a container may not be filled with blood even though it has been expanded to its maximum extent.

There are other types of collection or blood recovery bags that are configured with a spring type of mechanism to bias the bag open and keep it open when suction conditions are established within the bag. This allows blood to be drawn out of the body cavity and into the collection bag. These internal spring mechanisms act on the interior surfaces of the collection bag to keep the bag open under suction pressure conditions.

For example, one application of an internal spring mechanism consists of a metal spring acting on two opposing plastic members that in turn act on the opposing inside surfaces of the bag. Additionally, the plastic members are usually configured with a latching mechanism to keep the spring compressed so as to minimize the size of the collection bag for shipment and storage. Such types of collection bags are described in U.S. Pat. No. 4,429,693 granted to Blake et al. and U.S. Pat. No. 5,380,314 granted to Herweck et al.

Because internal spring members come into contact with the patient's blood, they must be manufactured of materials that do not pose a health risk or lead to blood contamination. Additionally, these internally located members can cause mechanical trauma to the blood being collected and/or re-infused. Thus, these members must be particularly constructed and configured so as to minimize such mechanical trauma.

When blood is being re-infused, it is desirable to be able to gravity feed the collected blood from the collection bag to a re-infusion device or directly to the patient. Typically blood bags for transfusion or other such fluid filled bags in a hospital or treatment facility are configured so that the fluid can be withdrawn from the bag and infused into the patient by gravity without requiring the bag to be vented. In order to withdraw fluid from a collection bag with an internal spring mechanism, however, the bag must be vented so the collected fluid can be gravity feed to the re-infusion device or patient.

Venting involves configuring the bag with another port that remains sealed while the blood is being collected. This vent is then opened while the blood is drained out of the bag. Additionally, to minimize blood contamination, the vent includes a filter member to filter the air before it enters the collection bag. In any event, the admission of air into the collection bag during re-infusion raises the concern of entrapping air or air bubbles in the blood being re-infused along with the related medical concerns if such blood were re-infused into the patient's circulatory system. Furthermore, if the vent is inadvertently left open or partially open while collecting blood, then the suction device may not suction the blood properly into the bag and may also create conditions involving the entrainment of the air in the collected blood.

Alternatively, a user could apply an external force to overcome the spring instead of venting the bag. However, the spring mechanism typically employs a spring that develops a relatively large force and a user does not easily overcome this force. This is particularly a problem considering the relatively small size and fluid capacity of the collection bag which may be about 700 ml or less and a force applied to such bags may be on the order of a 30 pound force. In addition, these types of bags do not lend themselves to the use of a pressure cuff where a user may apply an external force to the blood bag by means of a pressure cuff to force the blood out of the bag and under pressure.

As noted above, the plastic members that constitute a part of the spring mechanism typically include a latching mechanism so the spring is held in a compressed state and to hold the bag in a collapsed condition for purposes of shipping and storage. Because the latching mechanism is designed for easy actuation by a user, it is not uncommon for the latching mechanism to release during shipment, while they are being handled and/or while they are in storage. When the latching mechanism is released, the spring automatically opens the collection bag. Therefore, once the spring has been triggered by the release of the latching mechanism, it is very difficult, and in some cases impossible, to re-collapse the bag and re-latch the latching mechanism. For example, the latch may be designed as a single use device and may break when it is inadvertently released so the device cannot be re-latched. The presence of a foreign object within the collection bag may also make the bag unsuitable for other uses.

Other devices or apparatuses that are used for to evacuate or drain a wound by suction means and for blood collection and transfer are shown in U.S. Pat. Nos. 4,559,035, 4,443,220, 4,161,179, 3,993,067 and 4,424,053.

It thus would be desirable to provide a new collection bag or device and methods for collecting and re-infusing blood. It would be particularly desirable to provide such a collecting device and method that would minimize mechanical trauma to the collected and re-infused blood in comparison to prior art devices and allow blood to be easily re-infused by gravity or pressure feed without requiring simultaneous venting of the collection device. It is also desirable to provide such a device that minimizes the risk of inadvertent actuation during shipment, handling or storage as compared to prior art devices. Such collection devices are preferably simple in construction and less costly than prior art devices and use simple methods to utilize the device.

SUMMARY OF THE INVENTION

The present invention features a rapid transfer autotransfusion device and a system using such a device. Also featured are methods related to the collection and/or the re-infusion of collected blood to a patient. Such a device allows a user to quickly and easily set up the device so it can be used with an external drainage device to collect the blood and, upon completion of the collection, is easily re-configured so the collected blood can be re-infused into the patient. Although such a device is easily setup by a user for use, the device is configured so it is not readily susceptible to inadvertent triggering during shipment, handling or storage.

An autotransfusion device according to one aspect of the present invention includes a n actuator handle assembly having two arms, a top plate, a bottom plate and a flexible container secured to and between opposing surfaces of the top and bottom plates. T he bottom plate includes a projection from two opposing sides of the bottom plate so that each side rotatably engages a lower portion of an arm of the actuator handle. In this way, the actuator handle can rotate about the bottom plate projections between a first position and a second position.

The actuator handle further includes a follower member having first and second portions, and a displacing mechanism that is disposed in at least one actuator handle arm. In a more particular embodiment, a displacing mechanism is disposed in each actuator handle arm. The first portion of each follower member moveably engages a portion of the top plate as the actuator handle moves between the first and second position. The displacing mechanism is configured to act on the second portion of the follower member when the actuator handle is moved to the second position so the follower member first portion is displaced thereby to cause the top plate to be displaced with respect to the bottom plate.

In a second aspect of the present invention, the rapid transfer autotransfusion bag includes a top and bottom plate each configured so as to have a localized and complementary depression in the opposing surfaces thereof. The flexible container and the top and bottom plates are arranged so the depressions are in opposition to each other particularly when the top and bottom plates are proximate to each other. In this way, a space is formed between the localized depression on the top plate and the localized depression on the bottom plate along the inner surface of the flexible container.

The flexible container also includes a nozzle extension member disposed in fluid communication with the interior of the flexible container and a nozzle of the flexible container. The flexible container and the top and bottom plates are further arranged so the nozzle extension member is disposed in the space within the flexible container formed between and defined by the localized depressions in the top and bottom plates. In a more specific embodiment, the nozzle extension member includes a plurality of through apertures that are spaced along the long axis of the extension member. These apertures are in fluid communication with the interior of the flexible container and the nozzle.

A rapid transfer autotransfusion bag having an arrangement according to the preferred form of the present invention, preferably assures that a flow channel is present within the flexible container even when the top and bottom plates are proximate or abutting one another. Additionally, the plurality of apertures on the nozzle extension member provides a means for effectively maintaining a flow path into the flexible container. The apertures are also preferably arranged so any air within the flexible container can be effectively vented therefrom during a priming operation.

In another aspect of the present invention, the actuator handle for the rapid transfer autotransfusion bag is arranged with at least one latching mechanism and preferably one latching mechanism for each displacing mechanism. This allows the displacing mechanism(s) to be preloaded or "cocked" before the rapid transfer autotransfusion bag is put to use. More preferably, this type of latching mechanism is configured so that the displacing mechanism may be preloaded by the manufacturer prior to shipment of the autotransfusion bag to the user. Such a latching mechanism is also preferably configured so the displacing mechanism is not de-latched until the actuator handle is at least initially moved from the first position towards the second position. More preferably, the latching mechanism is configured so the de-latching step does not occur until the actuator handle is rotated a significant distance from the first position. This minimizes the potential for inadvertent actuation during shipment and/or routine handling of the rapid transfer autotransfusion bag. Additionally, in the preferred form of this invention, the actuation handle is removable from the autotransfusion bag by returning the handle towards the first position.

Other aspects and embodiments of the preferred form of the present invention are discussed below.

DEFINITIONS

The instant invention is most clearly understood with reference to the following definitions:

Autotransfusion shall be understood to mean the collection of a patient's blood and the subsequent step of infusing the collected blood back into the patient.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein:

FIGS. 1A and 1B are top and bottom perspective views of a rapid transfer autotransfusion bag according to the present invention with the actuation handle in the stored position;

FIG. 5A is a plan view of a rapid transfer autotransfusion bag according to a second aspect of the present invention;

FIG. 5B is a side view of the rapid transfer autotransfusion bag of FIG. 5A with a partial breakaway of the actuator handle for clarity;

FIGS. 7A and 7B are plan and end views respectively of a top plate for a rapid transfer autotransfusion bag according to a second aspect of the present invention;

FIG. 9 is a perspective view of an actuator handle for a rapid transfer autotransfusion bag according to a third aspect of the present invention;

FIG. 10 is a cross-section view of the actuator handle of FIG. 9 taken along line 10—10 of FIG. 9;

FIG. 11 is a cross-section view of the actuator handle of FIG. 9 taken along line 11—11 of FIG. 9;

FIGS. 12 and 13 are illustrative views of the process for collecting blood using the rapid transfer autotransfusion bag of the present invention; and FIG. 14 is a schematic view of an autotransfusion blood collection system using the rapid transfer autotransfusion bag of the present invention.

DESCRIPTION OF THE PREFERRED EMBODIMENT

Figure 2:
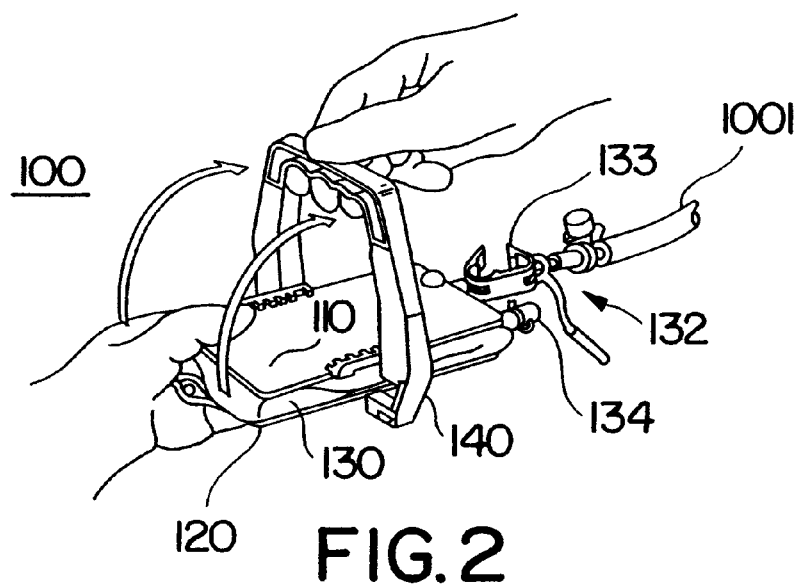
FIG. 2 is a perspective view of the rapid transfer autotransfusion bag of FIGS. 1 with the actuator handle in the blood collection position.

Referring now to the various figures of the drawings wherein like reference characters refer to like elements, there is shown in the Figures various views of a rapid transfer autotransfusion bag 100 according to the preferred form of the present invention generally illustrating the configurations of the autotransfusion bag and actuator handle at specific times during its use. Such an autotransfusion bag 100 includes an actuator handle 140 and a flexible bag assembly 102. The flexible bag assembly 102 includes a top plate 110, a bottom plate 120 and a flexible bag 130 that is secured to opposing surfaces of the top and bottom plates. The flexible bag 130 also includes an inlet spike or line 132, an outlet spike port or line 134 and an eyelet 136. The inlet line 132 also typically includes a conventional clamp 133 that selectively opens and closes the inlet line.

The top plate 110 is configured with two channel portions 112 or tracks and the bottom plate 120 includes a pivot pin 122 having two end portions 124. The channel portions 112 and the end portions 124 of the pivot pin are disposed on opposing sides, respectively, of the top plate 110 and the bottom plate 120. The actuator handle 140 is generally a U-shaped construction in which each leg portion thereof includes a lower portion 142. A follower member and a displacing mechanism are disposed in each actuator handle leg portion. The displacing mechanism acts on the follower member so as to move the top and bottom plates 110,120 apart from each other. Each lower portion 142 is rotatably secured to one of the pivot pin end portions 124 and a portion of each follower member is slidably disposed within one of the channel portions 112. The follower members and displacing mechanisms are described hereinafter.

As shown in FIGS. 1A and 1B, the actuator handle 140 is initially in a home or first position, where the top and bottom plates 110,120 of the flexible bag assembly 102 are proximate to each other and preferably, generally parallel to each other and where the flexible bag 130 is in its pre-collection or collapsed condition. This also is the configuration of the rapid transfer autotransfusion bag prior to use. In this configuration, the displacing mechanism does not act on the follower member and thus the top and bottom plates 110,120 also do not move apart from each other. As such, and in contrast to prior art collection bags, the autotransfusion bag 100 of the present invention cannot be actuated or opened inadvertently by a sharp force or impact such as may occur during shipment or handling.

To actuate the displacing mechanism and to collect blood, the actuator handle 140 is rotated about the pivot pin 122 of the bottom plate 120 which in turn causes a portion of each follower member to slidably move in the corresponding channel portion 112 on the top plate 110. When the actuator handle 140 is rotated toward the second position, the displacing mechanism acts on the follower member to move an end thereof toward the displaced position. In a specific embodiment, the actuation of the displacing mechanism occurs as the actuator handle 140 is rotated so that it is in the upright condition as shown in FIG. 2 or rotated about 90° from the home or first position to the second position.

As a consequence, and because of the mechanical connection between each follower member and each channel portion 112 and between each handle lower portion 142 and each pivot pin end portion 124, the displacing mechanism concurrently causes the top plate 110 to move away from the bottom plate 120. Although the present invention is illustrated and described as moving the top plate with respect to the bottom plate, it is within the scope of the present invention for a rapid transfer autotransfusion bag of the present invention to be configurable so the bottom plate moves with respect to the top plate or in a combination of these described movements.

Thereafter, blood is collected in the flexible bag 130 via the inlet line 132 and the flexible bag or container expands outwardly responsive to the inflow of blood and the displacing mechanism.

Figure 3:
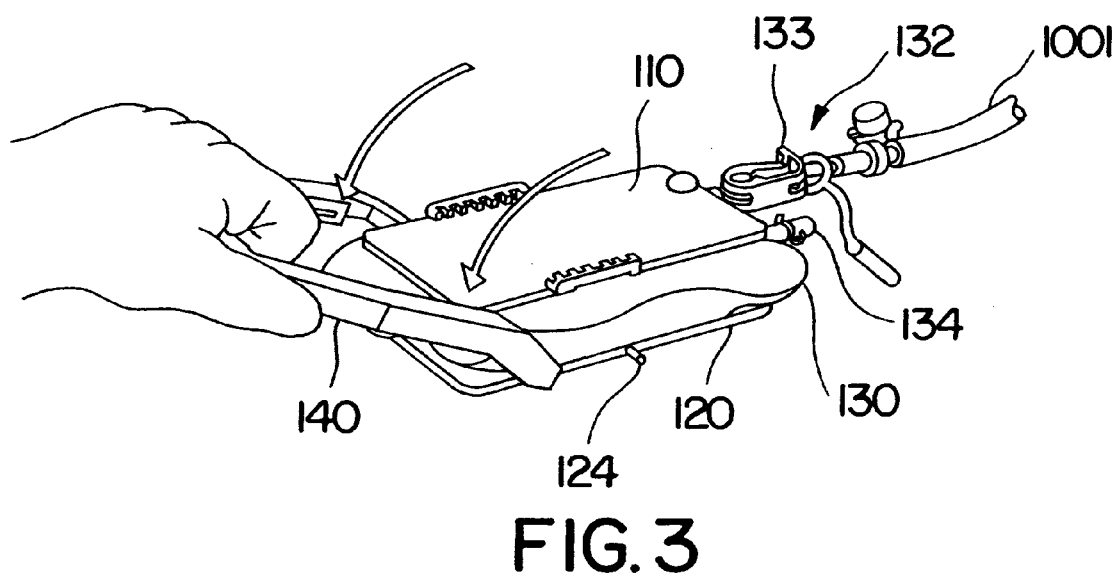
FIG. 3 is a perspective view of the rapid transfer autotransfusion bag of FIGS. 1 with the actuator handle in the detached position.

Referring now to FIG. 3, when the flexible bag 130 is filled or otherwise intended to be used for re-infusion, a user again rotates the actuator handle 140 about the pivot pin 122 so the follower members disengage from the channel portions 112 on the top plate 110. The user also disengages the actuator handle lower portions 142 from the pivot pin end portions 124 so the actuator handle 140 is separated from the flexible bag assembly 102. In a specific embodiment, the user rotates the actuator handle 140 back to the home or first position to disengage the follower members and actuator handle lower portions from the flexible bag assembly 102 although it is readily anticipated that a configuration may be used wherein continued rotation of the actuator handle 140 about the pivot pin 122 may cause the release of the actuator handle.

Although the top and bottom plates 110,120 and the corresponding channel portion 112 and end portions 124 of the pivot pin provide a means for easily biasing the flexible bag 130 into an open or partial open condition to receive blood, they do not impose limitations on, or impediments to, the subsequent re-infusion of blood into a patient using the flexible bag assembly 102. As such, after the actuator handle 140 is disengaged, a user can hang the flexible bag assembly 102 from a conventional IV hanger by means of the eyelet 136 (FIG. 1A) provided in an end of the flexible bag 130. In this fashion, blood can be infused into the patient using the conventional gravity re-infusion technique. Alternatively, the user can re-infuse the blood using a conventional pressure re-infusion technique, for example by disposing the flexible bag assembly 102 in a pressure cuff like that done with conventional IV bags.

Figure 4A:
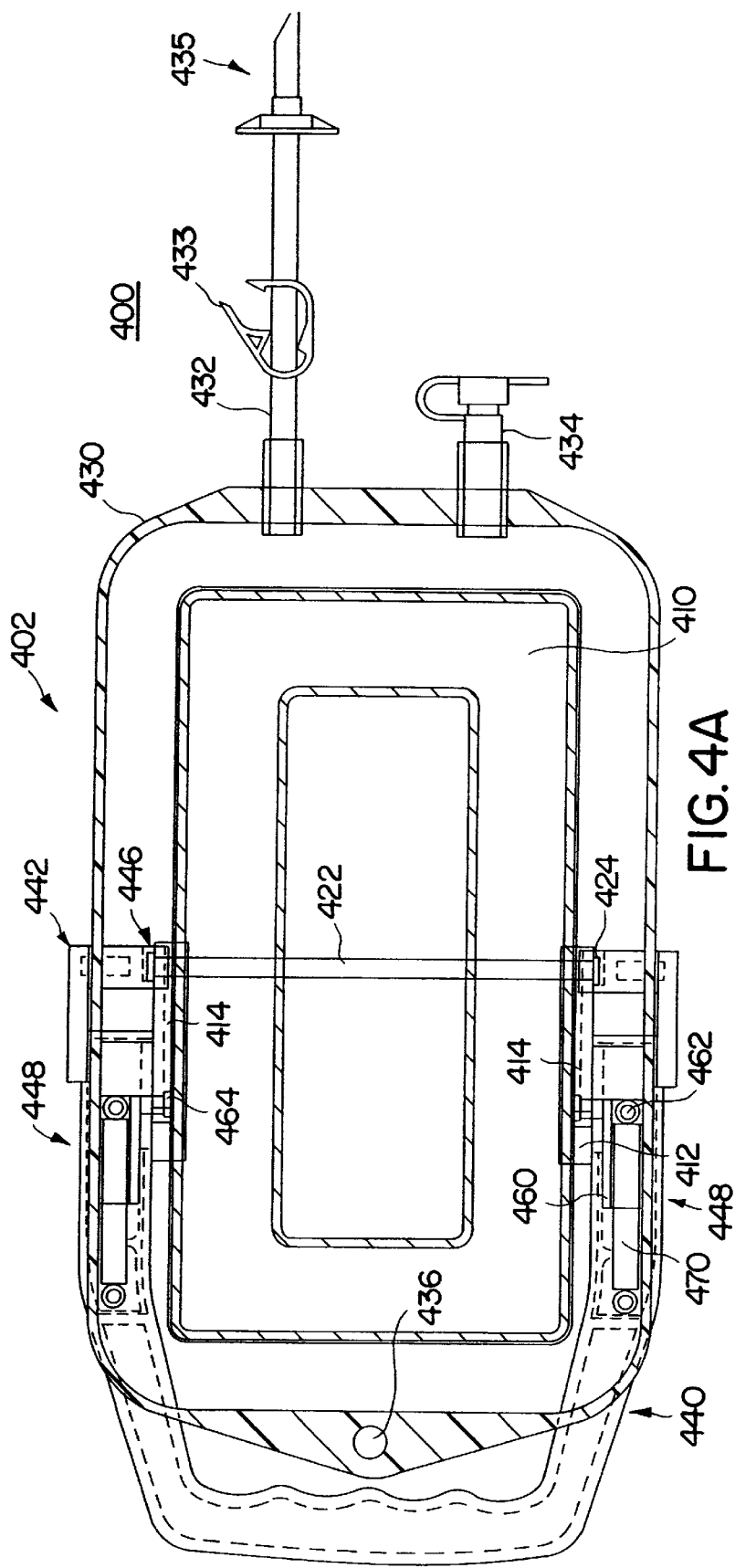
FIG. 4A is a plan view of a rapid transfer autotransfusion bag according to one aspect of the present invention.
Figure 4B:
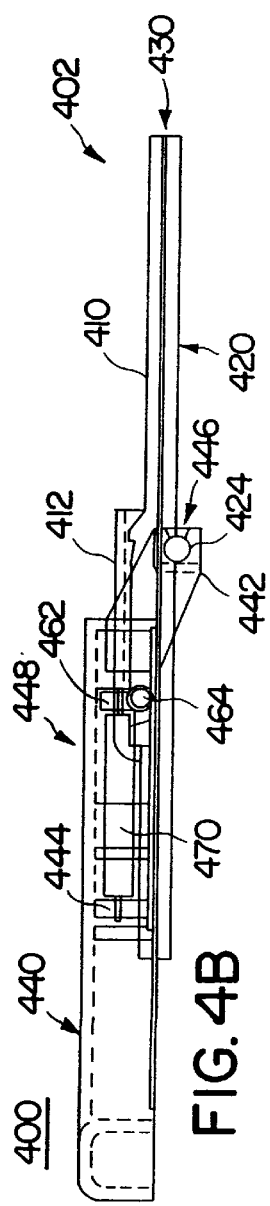
FIG. 4B is a side view of the rapid transfer autotransfusion bag of FIG. 4A with a partial breakaway of the actuator handle for clarity.
Figure 6A:
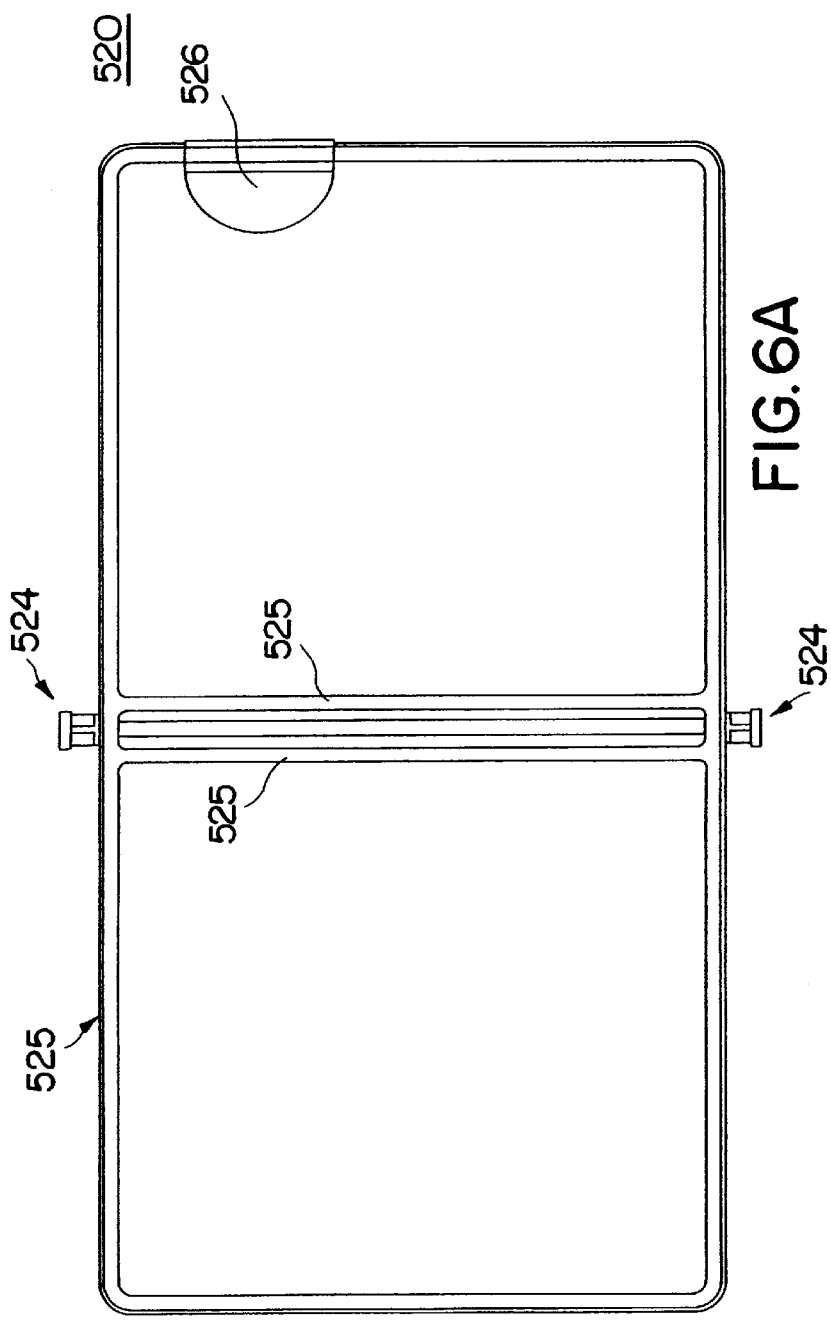
FIGS. 6A and 6B are plan and end views respectively of a bottom plate for a rapid transfer autotransfusion bag according to a second aspect of the present invention.
Figure 6B:
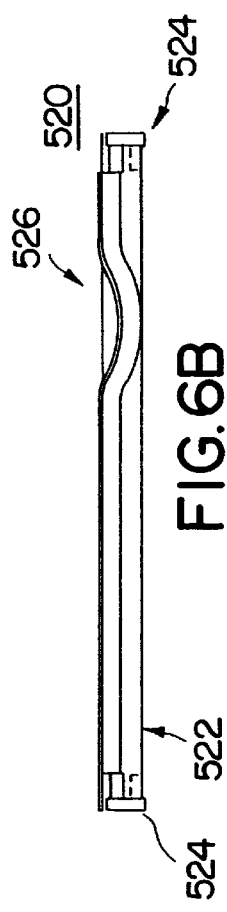

FIGS. 4A and 4B illustrate an embodiment of a rapid transfer autotransfusion bag 400 according to a first aspect of the present invention where the autotransfusion bag includes an actuator handle 440 and a flexible bag assembly 402. The flexible bag assembly 402 includes a top plate 410, a bottom plate 420 and a flexible bag 430 that is secured between the two plates.

The top plate 410 is a relatively rigid flat member including a plurality of channel portions 412 formed in a top surface and on opposite sides of the flat member. Similarly, the bottom plate 420 is a relatively flat member including a pivot pin 422 formed in a back surface of the flat member and extending across the width of the flat member and beyond the opposing sides thereof. The top and bottom plates 410,420 are constructed of a material having sufficient rigidity and strength to remain substantially flat when exposed to the loads imposed thereon by the negative internal pressure and the loads generated by the displacing mechanism, the springs 470. The materials of use also should be capable of meeting the sterility or cleanliness requirements of the intended use. In a specific embodiment, the top and bottom plates 410,420 are constructed of polyvinyl chloride (PVC).

The top and bottom plates 410,420 also can be configured with ridges, support ribs or other surface artifacts as known to those skilled in the art for stiffening the flat portions of the top and bottom plates. For example, support ribs can be arranged so as to be disposed about the circumference or outside edges of the top and bottom plates. Additionally, such support ribs also can be arranged so one or more traverse across the surface of each plate.

The flexible bag 430 of this embodiment includes an inlet line 432, an outlet line 434 and an eyelet 436 which, as described above, can be used to hang the flexible bag assembly 402 from an IV hanger so the fluid, i.e. blood collected therein can be re-infused using the gravity re-infusion technique. The inlet line is provided with a clamp 433 or other means known to those skilled in the art for selectively opening and closing the inlet line such as an in-line valve. Also, as shown in the illustrated embodiment, the inlet line 432 includes a spiked end 435.

The flexible bag 430, including the inlet and outlet lines 432, 434, are constructed of a material that is capable of satisfying the sterility or cleanliness requirements for collecting blood therein for later re-infusion into a patient. The material of use also is capable of being secured, affixed or bonded to the top and bottom plates 410, 420 using any of a number of techniques known to those skilled in the art thereby yielding a flexible bag assembly 402 according to the present invention. In a specific embodiment, the flexible bag 430 as well as the inlet and outlet lines 432, 434 are constructed of PVC and the flexible bag 430 is secured to the top and bottom plates 410,420 using an RF welding technique. The flexible bag 430 also is preferably secured to the top and bottom plates 410,420 (e.g., seal welded) so air does not leak between the flexible bag and a plate.

The following is illustrative of one technique using RF welding to assemble a flexible bag assembly 402 according to this or other aspects of the present invention. The top and bottom plates as illustrated in FIGS. 6A, 6B, 7A and 7B are preferably made of PVC and are placed parallel to and spaced from each other with the flat surfaces thereof facing up. A PVC film about 0.020 inches thick is laid over the flat surfaces and extended beyond the edges of the top and bottom plates. By means of RF welding, the PVC film is secured to the flat surface of the bottom plate in an area 525 along the outside edge of the plate and transverse to the outside edges on either side of the pivot pin 122. Similarly, the PVC film is secured to the flat surface of the top plate in an area 515 generally along the outside edge of the top plate. Additionally, the PVC film is spot welded to the notched segments of each top plate channel portion. Thereafter, the top and bottom plates are positioned so the flat surfaces thereof oppose each other with the PVC film disposed there-between. Then using any of a number of techniques available and known to those skilled in the art, the PVC film is processed further so as to form a flexible bag of the present invention.

The pivot pin 422 is formed or provided in the bottom plate 420 and includes two end portions 424. The pivot pin end portions 424 extend outwardly from opposite sides of the bottom plate 420 and are configured so each are rotatably received in a slotted pivot hole 446 provided in the lower portion 442 of each leg portion 448 of the actuator handle 440. The slotted pivot hole 446 and the pivot pin end portion 424 also are configured so the end portion is rotatably retained in the slotted pivot hole as the actuator handle 440 is rotated between the home or first position and a second position as described above. Additionally, the slotted pivot hole 446 and the pivot pin end portion 442 are configured so the end portion is removable from the slotted pivot hole, when the actuator handle 440 is again rotated in a specific direction to a given position such as when the position at which the actuator handle is disengaged from the flexible bag assembly 402. In one form of this invention, the pivot pin end portion includes a generally circular ridged portion wherein a portion of the ridged portion is flat to facilitate the placement of the pivot pin end portion 424 into the pivot hole 446. As noted above, in a specific embodiment, the actuator handle 440 may be rotated back to the home position to disengage the actuator handle 440 from the flexible bag assembly 402 although it is anticipated that a version of the present invention may allow for the continued rotation of the actuator handle to a releasable position.

The follower member 460 is slidably disposed in a passage provided in each actuator handle leg portion 448. The follower member preferably includes a main body member, a channel riding member 464 and a mounting pin 462. The passage is more clearly illustrated in FIG. 9. A spring 470 is also disposed in the passage and extends between a handle mounting pin 444 and the mounting pin 462. In this way, and as hereinafter described, the follower member 460 moves back and forth in the passage substantially along an axis defined by the mounting pins 444 and 462 and is responsive to the action of the spring 470. As illustrated in FIG. 1B, a cover is provided over the passage.

The spring 470 is configured so as to be capable of generating a sufficient force to move the top plate 410 away from the bottom plate 420 a sufficient distance so as to open the flexible bag 430 and to establish a negative pressure condition within the flexible bag. The spring 470 also is configured so as to keep the flexible bag 430 open while collecting blood. Because the springs 470 are advantageously external to the blood collection path, they can be constructed of a wide selection of materials. In contrast to prior art collection bags having internal spring devices that are in contact with the collected blood, the materials for the springs 470 of the present invention are not limited to materials that would not pose a health risk to blood collection or would not cause blood contamination. Additionally, the springs 470 of the present invention can have a wide range of configurations without regard to the mechanical trauma prior configurations may have on the blood being collected.

In a specific embodiment, each spring 470 is preferably a coil spring that is constructed from a zinc coated music wire. Additionally, the coil spring is configured such that the spring is capable of generating a force of about 8–10 pounds in the extended condition. Although a spring 470 is used as a mechanism for displacing the follower member 460 and thus the top plate 410, it is within the scope of the present invention to utilize any of a number of techniques and means for displacing the follower member in the manner herein described. For example, the displacing mechanism can be an elastomeric material like a shock cord or a gas piston type of cartridge.

The channel riding member 464 is essentially an extension of the main body member and is preferably orientated so as to be at a right angle with respect to the axis of motion of the spring 470 and the long axis of the follower member. The end of each channel riding member 464 also is configured so as to be slidably retained within a channel or track 414 provided in each top plate channel portion 412. In this way, when the actuator handle 440 is rotated about the pivot pin 422 from the first position to the second position, each channel riding member 464 correspondingly and slidably moves within the track 414.

As the actuator handle is rotated about the pivot pin 122 from the first position towards the second position, each spring 470 in the actuator handle 440 is extended lengthwise. This lengthwise extension of each spring 470 pre-loads or pre-tensions the spring to at least a desired value.

When the actuator handle 440 is in the second or upright position, each follower member 460 moves responsive to the restoring force of the pre-loaded or pretensioned spring 470. Correspondingly, the restoring force of at least one spring also causes the top plate 410 to move away from the bottom plate 420. This movement occurs because of the mechanical connection between the follower member 460 and the corresponding top plate channel portion 412. This motion of the top plate 410 with respect to the bottom plate 420 causes the flexible bag 430 to open to allow fluid to be received therein. Additionally, this motion establishes a negative pressure condition within the flexible bag 430 so as to cause the fluid to be drawn into the flexible bag.

Each track 414 in the top plate channel portion 412 is preferably configured so each channel riding member 464 of the actuator handle 440 can be disengaged from the corresponding top plate channel portion when the actuator handle 440 is rotated to a given position following the collection of blood within the flexible bag 430. In an exemplary embodiment, and as illustrated in FIG. 7A, an opening is provided in one end of each track 414 through which the channel riding member 464 can exit.

The follower member 460 and the actuator handle 440 are constructed or formed from any of a number of materials known to those skilled in the art that are capable of withstanding the loads being imposed during use and the expected environmental conditions. In a specific embodiment, the actuator handle 440 is made from acrylonitrile butadiene styrene (ABS) and the follower member 460 is made from acetal. Additionally, the actuator handle 440 can include surface artifacts and/or surface finishes or preparations that improve a user's grip or manipulation of the handle.

There is shown in FIGS. 5A and 5B another embodiment of a rapid transfer autotransfusion bag 500 according to a second aspect of the present invention that includes a flexible bag assembly 502 and an actuator handle 440. A flexible bag assembly 502 according to the second aspect is advantageously configured so a localized open space is maintained within the flexible bag 530, even when the top and bottom plates 510, 520 are generally proximate to or abutting each other as illustrated in FIG. 5B. Reference should be made to the foregoing discussion regarding FIGS. 4A and 4B for further details regarding the construction and materials for the actuator handle 460, the follower member 460 and spring 470 disposed therein of this embodiment. Also, reference should be made to that discussion regarding the general operation of the actuator handle 440 in connection with a flexible bag assembly to collect and re-infuse blood.

The flexible bag assembly 502 includes a top plate 510, bottom plate 520 and flexible bag 530. Each component is configured so as to provide additional assurances that blood or fluid will flow into the flexible bag 530 when it is initially opened and so the collected blood or fluid is efficiently drawn from the flexible bag during one of a gravity re-infusion or pressure re-infusion.

As more clearly illustrated in FIGS. 7A and 7B, the top plate 510 is configured or arranged so a portion 516 thereof forms a localized depression. In an illustrative embodiment, the localized depression has an arcuate sloping crosssection. The bottom plate 520 is similarly arranged, as more clearly shown in FIGS. 6A and 6B, so a portion 526 thereof forms a complementary localized depression having an arcuate sloping cross-section.

As described above, the flexible bag 530 is bonded or otherwise affixed to the top and bottom plates 510,520 so the flexible bag conforms to the shape of the plates. Thus, when the top and bottom plates 510, 520 are proximate to each other, as illustrated in FIG. 5B, a space is formed within the flexible bag 530 in the area of the localized depression of both the top and bottom plates 510,520. In this embodiment, these localized depressions 516,526 are preferably located so the space within the flexible bag 530 is in the area proximate and about the inlet line 532.

Figure 8:
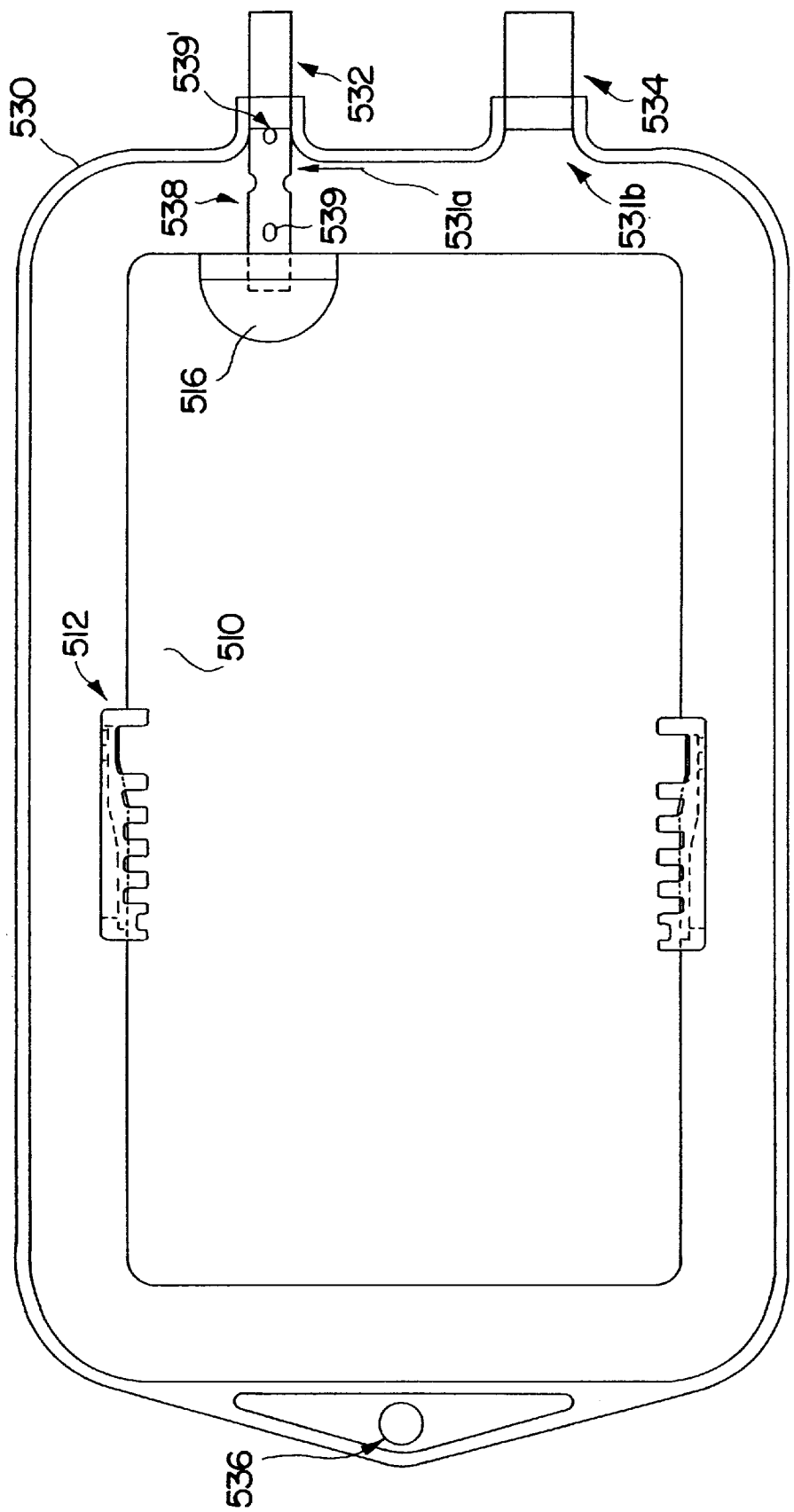
FIG. 8 is a plan view of the flexible bag assembly for a rapid transfer autotransfusion bag according to a second aspect of the present invention.

As more clearly shown in FIG. 8, the flexible bag 530 is configured so as to have two depressed regions, 531a and 531b, proximate and about the inlet and outlet lines 532, 534 and an internal nozzle extension 538 that is in fluid communication with the inlet line. The internal nozzle extension 538 is sized or has a length such that the outlet end thereof extends into the space within the flexible bag created by the localized depressions in the top and bottom plates 510 and 520. This assures that an unrestricted flow path is provided between the inlet line and the interior of the flexible bag 530 particularly when the bag is initially opened by the displacing mechanism or springs 470.

In specific embodiments, the internal nozzle extension 538 is configured with at least one through aperture and preferably a plurality of apertures located in the outer surface of the internal nozzle extension and along the length thereof. These apertures increase the flow area available for the passage of fluid into the flexible bag 530 so as to minimize the effect a blockage of one or more flow apertures would have on the inflow of the liquid or blood. Although only apertures on one side and along the long axis are illustrated, it is within the scope of the present invention for apertures to be located anywhere about the exterior surface. For example diametrically opposed apertures may be used in any arrangement along the long axis (e.g., staggered apertures on either side).

As described hereinafter, a user typically primes a blood bag to remove any air or gas that may be contained within the flexible bag 530. This can be accomplished in one case by orientating the flexible bag 530 so the inlet line 532 is generally upwardly disposed. Thus, the depressed region 531a in the flexible bag proximate the inlet line 532 provides a means for establishing a high point within the flexible bag in which air or gases would collect. Additionally, at least one aperture 539 may be located in the internal nozzle extension 538 so this aperture 539 communicates with the volume defined by the inlet line depressed region 531a whereby any gases or air collected therein can be removed during priming via the internal nozzle extension. In another case, a user could remove any air collected in the depressed region 513b proximate the outlet line 532 by means of the outlet line in a similar manner.

Similarly, when blood or fluid is being drawn from the flexible bag 530, for example by gravity re-infusion, the flexible bag is orientated so the outlet line 534 is orientated generally downwardly. Thus, the depressed region 531b proximate the outlet line assures that the maximum amount of collected blood or fluid can be withdrawn from the flexible bag 530.

A flexible bag 530 configured according to the present invention advantageously yields a fluid or blood collection bag in which the top and bottom plates, 510 and 520, in conjunction with the internal nozzle extension 538 establish a configuration so blood or fluid can be easily collected and the flexible bag may be easily primed for the removal of air. Such a flexible bag 530 also advantageously minimizes the wastage of collected blood by providing a means to effectively remove blood from the flexible bag.

As with the rapid transfer autotransfusion bag according to the first embodiment of the present invention, the front surface of the top plate 510 includes two channel portions 512 located on opposing sides and on the top surface thereof. These channel portions 512 include a track 514 that slidably receives the channel riding member 464 of the follower member 460. This channel or track 514 also includes an opening 513 (FIGS. 7A–C) at an end thereof through which the channel riding member 464 passes when the actuator handle 440 is to be disengaged from the flexible bag assembly 502.

Similarly, the back surface of the bottom plate 520 includes a pivot pin 522 having two end portions 524 that are configured so each can be rotatably received in a slotted pivot hole 446 provided in the lower portion 442 of each actuator handle leg portion 448. Each slotted pivot hole 446 and the pivot pin end portion 524 also are configured so as the end portion is rotatably retained in the slotted pivot hole as the actuator handle 440 is rotated between the home or first position and the second position as described above. Additionally, the slotted pivot hole and the end portion are configured so the end portion is removable from the slotted pivot hole, when the actuator handle 440 is again rotated in a specific direction to a given position so the actuator handle can be disengaged from the flexible bag assembly 502.

In more specific embodiments each end portion 524 includes or is formed with an eccentric or cam like lip. This eccentric or cam shaped lip rides in a channel 947 (FIG. 10) provided in each actuator handle lower portion 422 thereby retaining the end portions 524 within the slotted pivot hole. The pin segment of each portion 542 also can be configured or formed so as to have two diametrically opposed flat chord-like surfaces to assist with the disengagement of the actuator handle 440 from the end portions.

There is shown in FIG. 9 an actuator handle 940 and follower members 960 according to a third embodiment of the present invention. Cross-sectional views of portions of the actuator handle lower portion 942 are provided in FIGS. 10 and 11. As with the actuator handle according to the first embodiment, a spring 970 is interconnected between the actuator handle mounting pin 944 and the follower member mounting pin 962.

The actuator handle 940 and follower member 960 are particularly configured so the follower member can be latched in a fixed position within the actuator handle when the actuator handle is in the home or first position. When in the latched position, the springs 970 are extended lengthwise between the mounting pins 944 and 962, so each spring is pre-loaded or pre-tensioned to the desired load. Additionally, the actuator handle 940 and follower member 960 are configured so the follower member is de-latched and free to move responsive to the force of the spring 970 (FIG. 4A), when the actuator handle is rotated to the second position, for example the upright position. Such an actuator handle 940 and follower member 960 can be used with the flexible bag assembly 102, 402 or 502 of any of the embodiments of the present invention.

To accomplish such latching/de-latching, the actuator handle 940 includes a latching member 950 that is formed or provided in a surface of the passage in the actuator handle leg portion 948. When the actuator handle 940 is in the home or first position, each follower member 960 is preferably disposed within the actuator handle so the latching member 950 engages an opening or notch 968 in the main body 966 of the follower member 960. In this way, the follower member 960 is secured or latched from motion within the actuator handle 940. Preferably, in the manufacturing process, the spring 970 between the mounting pins 944 and 962 is pre-loaded by stretching or compressing it and the spring is retained in this pre-loaded or pre-tensioned condition by latching the follower member 960 as described above. The follower member 960 remains in its latched condition as the actuator handle 940 is rotated from the first position to a specific position, the second position, when the follower member is de-latched.

As described above, and also with reference to FIG. 7A, as the actuator handle 940 is rotated from the first position into the second position, the follower member channel riding member 962 rides or travels in a track 514 in each top plate channel portion 512. In an exemplary embodiment, the track 514 is configured so the channel riding member 962, as it follows the travel path, causes the follower member 960 to become de-latched from the latching member 950. For example, the track 514 can be configured so as to cause the channel riding member and correspondingly the follower member main body 966 to be displaced laterally so the latching member 950 essentially slips out of the notch 968. Preferably, the track 514 is configured so this disengagement may occur when the actuator handle 940 is rotated to or reaches the second or upright position.

When the follower member 960 is disengaged from the latching member 950 or de-latched, the pre-loaded springs 970 act on the top plate 510 and move the follower member 960 away from the bottom plate 520 as described above. Such a latching/de-latching mechanism advantageously assures that the spring is not actuated until and when the flexible bag 530 is prepared to collect blood and to establish the negative pressure condition desired for the blood collection. By positioning the springs 970 in an extended condition, this mechanism also makes it easier for a user to rotate the actuator handle 940 from the home position to the second position.

As noted above, FIGS. 10 and 11 are cross-section views of the actuator handle 960 that illustrate the slotted pivot hole 946 that slidably and rotatably receives the pivot pin end portions 524. As indicated above, a channel 947 is provided for each slotted pivot hole 946 and each channel 947 rotatably receives the lip of each end portion. Each channel 947 and slotted pivot hole 946 also include a slot or opening therein so the pivot pin and lip thereof can be received therein.

The rapid transfer autotransfusion bag according to the present invention can advantageously collect blood from any of a number of drainage devices or systems known in the art for removing blood from a body cavity, particularly when such a device or system is still connected to the patient. The types of devices or systems that are useable includes those which employ a water manometer and water patient seal such as the Pleur-evac® A-9350 Continuous Reinfusion Autotransfusion System made by Genzyme Surgical Products. Also included are devices or systems that employ a waterless suction pressure regulating means and a water patient seal such as the Pleur-evac® A-9250 Continuous Reinfusion Autotransfusion System made by Genzyme Surgical Products and including U.S. Pat. Nos. 4,784,642, 5,507,734 and 5,026,358 the teachings of which are incorporated herein by reference. Additionally, there are included devices and systems that employ a waterless suction pressure regulating means and a dry or waterless patient seal such as the Pleur-evac® Sahara S-1150 Continuous Reinfusion Autotransfusion System made by Genzyme Surgical Products and including those systems or devices described and disclosed in U.S. Pat. Nos. 4,738,671, 4,715,856, 4,544, 370 and 4,747,844 and U.S. Ser. No. 08/783,177 the teachings of which are incorporated herein by reference.

The following discussion with reference to the Figures, describes the use of a rapid transfer autotransfusion bag 100 of the present invention with an autotransfusion drainage device of the type disclosed in U.S. Ser. No. 08/783,177 so as to form an autotransfusion system 1000. The autotransfusion drainage device 1002 illustrated in FIGS. 13 and 14 is exemplary and thus, it is within the scope of the present invention for the rapid transfer autotransfusion bag 100 to be used in conjunction with any of a number of blood collection or drainage devices known to those skilled in the art as herein above-described.

To set up the autotransfusion system 1000, a user removes the rapid transfer autotransfusion bag 100 from its protective packaging so it is available for use. The rapid transfer autotransfusion bag 100 is configured with the actuator handle 140 initially in the home position and also preferably with the flexible bag inlet line clamp 1003 open. Before connecting the rapid transfer autotransfusion bag 100 to the autotransfusion drainage device 1002, the user typically closes the clamp 1003 in the output or reinfusion line 1001 from the autotransfusion drainage device. The user then inserts the spiked end 135 of the flexible bag inlet line 132 into the reinfusion line 1001, thereby establishing the autotransfusion system 1000 as shown in FIG. 14. Typically, the user also opens the reinfusion line clamp 1003 after interconnecting the inlet line 132 and the reinfusion line 1001.

Additionally, and to optimize blood flow, a user also may adjust the suction pressure being developed within the draining device or system, for example to a suction pressure not greater than 20 cm $H_2O$. Also, a user may position the autotransfusion bag 100 so it is below the level of the collection chamber of the autotransfusion drainage device 1002.

As noted above, some draining devices, such as the autotransfusion drainage device 1002 illustrated herein, employ a dry or non-fluid patient seal. To improve the efficiency of drawing blood from the autotransfusion drainage device 1002 as well as the time taken to draw done the collected volume, a relief valve 1004 is fluidly interconnected to the collection chamber of the autotransfusion drainage device. For example, an 18-gauge needle is secured to the relief valve inlet and the needle is inserted into the self-sealing diaphragm of the autotransfusion drainage device 1002. In a specific embodiment, the relief valve is configured so it opens to admit air into the autotransfusion device 1002 if the pressure within the collection chamber falls below about −10 cm of $H_2O$ and closes when the pressure is at or above about −5 cm of $H_2O$. The set points for the relief valve are preferably set so the body cavity of the patient that is connected to the autotransfusion drainage device 1002, does not reach to atmosphere. For autotransfusion drainage devices or systems that employ a water or fluid patient seal, air can be drawn into the collection chamber through the patient seal as the volume of blood is being removed from the collection chamber by the rapid transfer autotransfusion bag 100.

After the autotransfusion system 1000 is configured to begin the collection of blood and thus ready for use, the user verifies that the re-infusion line clamp 1003 is opened and gently lifts/rotates the actuator handle 140 to the upright locked position to begin blood transfer as is illustrated in FIG. 2. As described above, when the actuator handle is rotated to the upright position, the springs move the top plate 110 away from the bottom plate 120, thereby opening the flexible bag 130 and establishing a negative pressure condition within the flexible bag. When so activated, blood is drawn into the flexible bag 130 from the collection chamber of the autotransfusion drainage device 1002. As the blood is drawn into the flexible bag 130, the flexible bag expands outwardly and the top plate 110 continues to be displaced with respect to the bottom plate 120.

Typically, the transfer of blood from the collection chamber is terminated prior to drawing air from the drainage device or system or when the desired volume has been withdrawn. When the transfer of blood is completed, the user closes both the reinfusion line clamp 1003 and the inlet line clamp 133.

Thereafter, and as illustrated in FIG. 3, the user then rotates the actuator handle 140 back towards the home position so the actuator handle can be disengaged from the flexible bag assembly 102. After the actuator handle 1040 is removed, it is discarded in accordance with accepted practices. Typically, the user also determines the liquid level or fluid volume within the flexible bag assembly 102.

If desired, a user may re-open the clamps 133,1003 and prime the flexible bag assembly 102 using the re-infusion line 1001 and the drainage device 1002 to receive the air. After priming, the user may re-close the clamps 133, 1003. After the actuator handle 140 is removed, and after any priming, the user removes the inlet line spiked end 135 from the reinfusion line 1001 so the rapid transfer autotransfusion bag 100 is disconnected from the autotransfusion drainage device 1002. Alternatively, a user may disconnect the rapid transfer autotransfusion bag 100 from the reinfusion line 1001 before removing the actuator handle.

A user may then insert a microaggregate filter (not shown) into the spike port of the outlet line 134 and attach an infusion set (not shown) to the microaggregate filter. Residual air also is evacuated from the flexible bag assembly 102 and the filter is primed, for example by gently squeezing the flexible bag assembly until the filter is saturated with blood. Thereafter, and by appropriately closing and opening of clamp(s), the flexible bag assembly 102 can be suspended from a conventional IV pole so the collected blood can be reinfused by gravity reinfusion. Alternatively, the flexible bag assembly 102 can be used with a pressure cuff so the blood is reinfused by pressure reinfusion. After the blood in the flexible bag assembly 102 has been reinfused, the flexible bag assembly is discarded in accordance with normal practices.

After the rapid transfer autotransfusion bag 100 is disconnected from the autotransfusion drainage device 1002, the user removes the relief valve 1004. In addition and if necessary, the user returns the autotransfusion drainage device 1002 to the desired operating conditions for the collection of blood from the patient's body cavity. Thereafter, the foregoing process is repeated as and when necessary to withdraw any further collected blood from the autotransfusion drainage device.

Although the preferred embodiments of the invention have been described using specific terms, such description is for illustrative purposes only, and it is to be understood that changes and variations may be made without departing from the spirit or scope of the following claims.

What is claimed is:

1. An autotransfusion device comprising:

an actuator handle assembly having a plurality of arms;

a top member;

a bottom member;

a flexible container secured to opposing surfaces of the top and bottom members;

wherein the bottom member includes a projection that rotatably engages a one of the plurality of arms of the actuator handle assembly, where the actuator handle assembly rotates about the bottom member projection between a first position and a second position wherein the top and bottom members are generally adjacent to each other in the first position and are generally spaced apart from each other in the second position;

wherein the actuator handle assembly further includes a follower member, having a first and a second portion, and a displacing mechanism that are disposed in at least one of the arms;

wherein the first portion of the follower member moveably engages a portion of the top member as the actuator handle assembly moves between the first and second position; and wherein the displacing mechanism is configured to act on the second portion of the follower member at least when the actuator handle is moved between the first and second positions so the follower member first portion is displaced thereby and so the top member opposing surface is displaced with respect to the bottom member opposing surface in the second position.

2. The autotransfusion device of claim 1, wherein a follower member and displacing mechanism is disposed in each actuator handle arm.

3. The autotransfusion device of claim 1, wherein the displacing mechanism includes a spring member one end of which contacts the second portion of the follower member.

4. The autotransfusion device of claim 1, wherein the actuator handle assembly is removable from the flexible container in the second position.

5. The autotransfusion device of claim 1, wherein a lower portion of each actuator handle arm is configured so the actuator handle assembly is rotatable from the second position to a position where the lower portion disengages the bottom member projection thereby allowing the actuator handle assembly to become detached from the top and bottom members.

6. The autotransfusion device of claim 1, wherein the displacing mechanism includes a latching mechanism that releasably secures the follower member so the follower member is held in a fixed position when the actuator handle assembly is in the first position and so the follower member is released from the latching mechanism at least when the actuator handle assembly is in the second position.

7. The autotransfusion device of claim 6, wherein the top member includes a track thereon and wherein the track includes a tripping member and wherein the latching mechanism is released responsive to passage of the follower member past the tripping member.

8. The autotransfusion device of claim 1, wherein the actuator handle assembly further includes a handle and two actuator assemblies interconnected to the handle so as to form a portion of the actuator handle arms, wherein the follower member and displacing mechanism are disposed within each actuator assembly and wherein the bottom member projection rotatably and releasably engage a pivoting mechanism of the actuator assembly.

9. The autotransfusion device of claim 8, wherein the handle and actuator assemblies form a substantially U-shaped structure.

10. The autotransfusion device of claim 1, wherein:
the flexible container includes a through port in which blood flows into the flexible container;
the port includes a hollow internal extension member through which blood flows; and
wherein the internal extension member includes at least one through aperture that extends perpendicular to a long axis of the internal extension member.

11. The autotransfusion device of claim 10, wherein the internal extension member includes a plurality of through apertures being spaced from each other along the long axis.

12. The autotransfusion device of claim 10, wherein the internal extension member includes a plurality of through apertures being spaced from each other radially about the long axis.

13. The autotransfusion device of claim 10, wherein the top and bottom members include a localized depression in the opposing surfaces, the local depression being proximate at least a portion of the internal extension member and wherein the depression is configured so a space is established between an outer surface of the internal extension member and an inner surface of the flexible container when the opposing surfaces of the top and bottom members are proximate to each other.

14. The autotransfusion device of claim 13, wherein the depression is configured so the space established between the internal extension member outer surface and the flexible container inner surface extends at least a portion of a length of the internal extension member.

15. The autotransfusion device of claim 13, wherein the internal extension member includes a plurality of through apertures being spaced from each other along the long axis and wherein the depression is configured such that at least one of the through apertures communicates with the space established between the internal extension member outer surface and the flexible container inner surface.

16. The autotransfusion device of claim 8, wherein the pivoting mechanism is configured so the bottom member projection is released by the pivoting mechanism when the actuator handle assembly is returned towards the first position.

17. An autotransfusion device comprising:
a top member having a track portion proximate two opposing sides thereof;
a bottom member having a projection extending from two opposing sides thereof;
a flexible container secured to and between opposing surfaces of the top and bottom members;
a removable actuator handle assembly including:
a plurality of arm portions,
a follower member disposed in at least one of the arm portions and having a first and second portion,
a displacing mechanism which is operatively secured to the said at least one actuator handle arm portion and engaging the follower member second portion,
a pivoting mechanism being disposed at a lower end of each of the arm portions, wherein the bottom member projection is rotatably received in the pivoting mechanisms so the actuator handle assembly rotates about the bottom member projections between a first position and a second position, and
wherein the pivoting mechanism is configured so as to disengage the bottom member projections when the actuator handle assembly is rotated a certain direction and whereby the actuator handle assembly is detachable from the top and bottom members; and
wherein the displacing mechanism is configured to act on the follower member second portion at least when the actuator handle is moved to the second position and so the follower member first portion act on the top member so as to move the top member opposing surface in a direction away from the bottom member opposing surface.

18. The autotransfusion device of claim 17, wherein the displacing mechanism includes a latching mechanism that releasably secures the follower member so the follower member is held in a fixed position when the actuator handle assembly is in the first position and so the follower member is released from the latching mechanism at least when the actuator handle assembly is in the second position.

19. The autotransfusion device of claim 18, wherein the top member includes a track portion having a tripping member thereon so the latching mechanism is released responsive to the tripping mechanism.

20. The autotransfusion device of claim 17, wherein:
the flexible container includes a through port through which blood flows into the flexible container;
the port includes a hollow internal extension member through which blood flows; and
wherein the internal extension member includes at least one through aperture that extends perpendicular to a long axis of the internal extension member.

21. The autotransfusion device of claim 20, wherein the internal extension member includes a plurality of through apertures being spaced from each other along the long axis.

22. The autotransfusion device of claim 20, wherein the internal extension member includes a plurality of through apertures being spaced from each other radially about the long axis.

23. The autotransfusion device of claim 20, wherein the top and bottom members include a localized depression in the opposing surfaces, each localized depression being proximate at least a portion of the internal extension member and wherein each localized depression is configured so a space is established between an outer surface of the internal extension member and an inner surface of the flexible container when the opposing surfaces of the top and bottom members are proximate to each other.

24. The autotransfusion device of claim 23, wherein the internal extension member includes a plurality of through apertures being spaced from each other along the long axis and wherein the depression is configured so at least one of the through apertures communicates with the space established between the internal extension member outer surface and the flexible container inner surface.

25. An autotransfusion method comprising the steps of;
providing an autotransfusion device including:
an actuator handle assembly having two arms,
a top member,
a bottom member,
a flexible container secured to and between opposing surfaces of the top and bottom members, wherein the flexible container includes at least one port,
wherein the bottom member includes a projection extending from each of two opposing sides of the bottom member, that each rotatably engage a lower portion of an arm of the actuator handle assembly, where the actuator handle assembly rotates about the bottom member projections between a first position and a second position,
wherein the actuator handle assembly further includes a follower member, having a first and a second portion, and a displacing mechanism that is disposed of the actuator handle arms,
wherein the first portion of each follower member movably engages a portion of the top member as the actuator handle assembly moves between the first and second position, and
wherein the displacing mechanism is configured to act on the second portion of the follower member at least when the actuator handle is moved to the second position so the follower member first portion is displaced thereby and so the top member opposing surface is displaced with respect to the bottom member opposing surface; and
first rotating the actuator handle assembly with respect to the flexible container from the first position to the second position, thereby opening the flexible container so fluids can be collected therein.

26. The autotransfusion method of claim 25, further comprising the step of rotating the actuator handle assembly and detaching the actuator handle assembly from the top and bottom members.

27. The autotransfusion method of claim 26 further comprising the step of creating a negative pressure in the flexible container and withdrawing fluid from the body cavity into the flexible container after the step of rotating the actuator handle assembly from the first position and towards the second position.

28. The method of claim 27, wherein the fluid being collected in the flexible container is blood and in which the method further comprises the step of re-infusing the blood into the patient following the step of detaching the actuator handle assembly from the top and bottom members.

* * * * *

UNITED STATES PATENT AND TRADEMARK OFFICE
CERTIFICATE OF CORRECTION

PATENT NO. : 6,210,391 B1
DATED : April 3, 2001
INVENTOR(S) : Kevin M. Lord

It is certified that error appears in the above-identified patent and that said Letters Patent is hereby corrected as shown below:

Title page,
References Cited, U.S. PATENT DOCUMENTS, add the following references:
-- 5,352,218    10/94    Buckley et al.
   5,380,314    1/95     Herweck et al.
   5,456,824    10/95    Misumi et al.

Column 19,
Line 33, replace "of the actuator handle arms," with -- in at least one of the actuator handle arms, --

Signed and Sealed this

Twenty-sixth Day of February, 2002

Attest:

JAMES E. ROGAN
Attesting Officer
Director of the United States Patent and Trademark Office